(12) United States Patent
Kozian et al.

(10) Patent No.: US 6,645,741 B2
(45) Date of Patent: Nov. 11, 2003

(54) TWO-COLOR DIFFERENTIAL DISPLAY AS A METHOD FOR DETECTING REGULATED GENES

(75) Inventors: Detlef Kozian, München (DE); Birgit Reuner, München (DE)

(73) Assignee: Aventis Pharma Deutschland GmbH, Frankfurt am Main (DE)

( * ) Notice: Subject to any disclaimer, the term of this patent is extended or adjusted under 35 U.S.C. 154(b) by 106 days.

(21) Appl. No.: 10/015,593

(22) Filed: Dec. 17, 2001

(65) Prior Publication Data

US 2002/0090636 A1 Jul. 11, 2002

Related U.S. Application Data

(62) Division of application No. 09/390,324, filed on Sep. 7, 1999, now Pat. No. 6,342,376.

(30) Foreign Application Priority Data

Sep. 7, 1998 (DE) .......................................... 198 40 731

(51) Int. Cl.$^7$ ........................... C12P 19/34; C12Q 1/68; G01N 33/00; C07H 21/02; C07H 21/04
(52) U.S. Cl. ........................ 435/91.2; 435/6; 435/91.1; 435/91.51; 436/94; 536/23.1; 536/24.33
(58) Field of Search .................... 435/6, 91.1, 91.2, 435/91.51, 183; 436/94; 536/23.1, 24.3, 24.33, 25.3, 25.32

(56) References Cited

U.S. PATENT DOCUMENTS

| 5,262,311 A | 11/1993 | Pardee et al. |
| 5,599,672 A | 2/1997 | Liang et al. |
| 5,665,547 A | 9/1997 | Pardee et al. |

FOREIGN PATENT DOCUMENTS

| DE | 195 18 505 | 11/1996 |
| WO | 93/18176 | 9/1993 |

OTHER PUBLICATIONS

McBride, L.J. et al., "An Investigation of Several Deoxynucleoside Phosphoramidites Useful for Synthesizing Deoxyoligonucleotides," Tetrahedron Letters, 24(3):245–248 (1983).
Smith N. R. et al., "Automated Differential Display Using a Fluorescently Labeled Universal Primer," BioTechniques, 23:274–279 (1997).
McClelland, M. et al., "RNA Fingerprinting and Differential Display Using Arbitrarily Primed PCR," Trends In Genetics, 11(6):242–246 (1995).
Liang, P. et al., "Differential Display of Eukaryotic Messenger RNA by Means of the Polymerase Chain Reaction," Science, 257:967 (1992).
Liang, P. et al., "Recent Advances in Differential Display," Current Opinion In Immunology, 7:274–280 (1995).
Jones, S.W. et al., "Generation of Multiple mRNA Fingerprints Using Fluoresence–based Differential Display and an Automated DNA Sequencer," BioTechniques, 22:536–543 (1997).
Ito, T. et al., "Fluorescent Differential Display: Arbitrarily Primed RT–PCR Fingerprinting on an Automated DNA Sequencer," FEBS Letters, 351;231–236 (1994).
Ito, T. et al., "Fluorescent Differential Display," Methods in Molecular Biology, 85:37–44 (1997).
Bauer, D. et al., "Identification of Differentially Expressed mRNA Species by an Improved Display Technique (DDRT–PCR)," Nucleic Acids Research 21(18):4272–4280 (1993).
Luehrsen K.R. et al., "Analysis of Differential Display RT–PCR Products Using Fluorescent Primers and GENES-CAN™ Software," BioTechniques, 22:168–174 (1997).
Smith, N.R. et al., "Automated Differential Display Using a Fluorescently Labeled Universal Primer," BioTechniques, 23(2);274–279 (1997).
Rigler et al., "Fluorescence Cross–Correlation: A New Concept for Polymerase Chain Reaction," J. Biotechnol. 63:97–109 (1998).

Primary Examiner—Ethan Whisenant
Assistant Examiner—Frank Lu
(74) Attorney, Agent, or Firm—Finnegan, Henderson, Farabow, Garrett & Dunner, L.L.P.

(57) ABSTRACT

The invention relates to a novel method for analyzing the composition of an mRNA sample and analyzing differential gene expression using two differently labeled primers, and to the use of the method.

In the method for analyzing an RNA sample,
 a) a first primer, which is, where appropriate, labeled with a first dye, is used to prepare the first strand of a complementary DNA sample or cDNA sample from an RNA sample,
 b) a second primer, which is preferably labeled with a second dye, is used to prepare the second strand of this cDNA sample,
 c) the first primer, which is labeled with a first dye, and the second primer, which is labeled with a second dye, are used to amplify the cDNA sample, and
 d) the composition of the amplified, labeled cDNA sample is analyzed.

18 Claims, No Drawings

TWO-COLOR DIFFERENTIAL DISPLAY AS A METHOD FOR DETECTING REGULATED GENES

This is a division of application Ser. No. 09/390,324, filed Sep. 7, 1999, now U.S. Pat. No. 6,342,376B1, which claims the benefit of German Patent Application No. 19840731.9, of Sep. 7, 1998, which is incorporated herein by reference.

FIELD OF THE INVENTION

The invention relates to a novel method for analyzing the composition of an mRNA sample and analyzing differential gene expression using two differently labeled primers, and to the use of the method.

BACKGROUND OF THE INVENTION

Differential RNA display (DD) is one of the methods most frequently used for detecting and isolating regulated genes (Liang, P. and Pardee, A. B. (1992) Science 257,967–971; Liang and Pardee (1995) Current Opinion in Immunology 7,274,280; McClelland et al. (1995) Trends in Genetics 11: 242–246). The Differential Display and Reverse Transcription (DDRT) method initially involves reverse transcribing isolated RNA using a first primer in a reverse transcription (RT) reaction, thereby preparing the first strand of a complementary DNA (cDNA). In the following step, this cDNA is amplified by the polymerase chain reaction (PCR) using the first primer and a second primer. The amplified cDNA sample is then analyzed, for example, by fractionating the amplified cDNA in a gel. Detection of the PCR product can be achieved, for example, by hybridizing with a labeled probe or by labelling the amplified cDNA. Detection can also be achieved by carrying out the amplification in the presence of radioactively labeled nucleotides, usually radioactively labeled dATP, or in the presence of a labeled primer which is, for example, labeled with a fluorescence ("fluorescence DDRT") (Ito et al. (1994) FEBS Letters 351, 231–236; Ito and Sakaki ("Methods in Molecular Biology Vol. 85: Differential Display Methods and Protocols" (1997) p. 37–44 Liang and Pardee eds., Human Press Inc. Totowa, N.J.; Jones et al. (1997) Biotechniques 22, 536–543; Smith et al. (1997) Biotechniques 23, 274–279).

If the reaction is carried out in the presence of radioactively labeled nucleotides, all the amplified cDNAs are then labeled. This technique is also known as radioactive DDRT or classical DDRT. If, on the other hand, a labeled primer is used (e.g. for fluorescence DDRT), only a part of the amplified cDNAs is labeled because of the possible primer combinations of the first labeled primer and of the second unlabeled primer during the PCR.

The first labeled primer, primer 1, is in this case, an oligo(dT) primer which possesses two further nucleotides (M=A, C, G; N=A, C, G, T) at the 3' end. Thus "5'-$(T)_{12}$-MN-3'" is equivalent to "$(T)_{12}$-MN." Labeled primer 1 is used in the RT reaction. The second unlabeled primer, primer 2, is in this case, an oligonucleotide which has a sequence of 10 randomly ordered nucleotides ("10 mer"). Labeled primer 1 and unlabeled primer 2 are used in the subsequent PCR; however, primer 1 is customarily used in a twofold excess. In this way, a relatively high proportion of amplified cDNAs whose 3' ends exhibit the sequence of the first primer and whose 5' ends exhibit the sequence of the second primer (e.g. 5–10 mer - - - $(T)_{12}$-MN-3', where "- - -" symbolizes the amplified cDNA sequence which is located between the primer sequences) is obtained as a rule.

The resulting PCR reaction potentially gives rise to four types of PCR products as listed below. The first product is as described above, where 3' ends exhibit the sequence of the first primer and 5' ends exhibit the sequence of the second primer (i.e. product 1). The second product contains primer sequences that are transposed as compared with product 1, at whose 5' and 3' ends can be found the sequences of the $(T)_{12}$-MN primer and of the 10 mer primer, respectively (i.e. product 2). Other cDNAs are either amplified only using the $(T)_{12}$-MN primer (i.e. product 3) or only using the 10 mer primer (i.e. product 4). Consequently, the use of two different primers can result in the amplification of the following reaction products in a DDRT as a result of the possible primer combinations:

Product 1) 5'-10 mer - - - $(T)_{12}$-MN-3'

Product 2) 5'-$(T)_{12}$-MN - - - 10 mer-3'

Product 3) 5'-$(T)_{12}$-MN - - - $(T)_{12}$-MN-3'

Product 4) 5'-10 mer - - - 10 mer-3'

Owing to the fact that only the first primer is labeled in this fluorescence DDRT, only those cDNAs which were amplified in at least one direction using the labeled first primer, products 1, 2, and 3, are detected in the subsequent analysis of the amplified cDNAs. In contrast, cDNAs which are only amplified using the second primer are neither labeled nor detected (i.e. product 4). Consequently, the complexity of the detected PCR products (cDNAs) is less than that in a radioactive DDRT. For this reason, the conventional fluorescence DDRT does not detect those regulated genes, or the mRNAs which correspond to them, which are only amplified using the second primer. As a result, the number of regulated genes detected by the conventional fluorescence DDRT can be lower than that detected in a radioactive DDRT.

Furthermore, when one single mRNA is used, a uniform cDNA product is not amplified in the PCR either with conventional radioactive DDRT or with conventional fluorescence DDRT, as shown above in products 1 to 4. Instead, several cDNAs which differ in their length, as seen by fractionating in a gel, can be amplified as a result of the different primer combinations. Only a detailed analysis such as direct sequencing would show whether different amplified cDNAs are cDNA products of one and the same regulated gene or not. The conventional DDRTs do not provide the possibility of differentiating between the redundant labeled, amplified cDNAs. In a radioactive DDRT, it is not possible to differentiate between products 1 to 4. In a conventional fluorescence DDRT, it is not possible to differentiate between products 1, 2, and 3 although there is a greater probability that the visible cDNA fragment derives from the 3' region of a gene since the 3' primer is labeled with the fluorescence dye.

Consequently, the redundancy of amplified cDNA fragments in conventional radioactive DDRT cannot be established or can only be established with a relatively large amount of effort. On the other hand, conventional fluorescence DDRT results in a lower complexity of the amplified cDNA product as compared with conventional radioactive DDRT. Furthermore, conventional fluorescence DDRT runs the risk of overlooking particular regulated genes. These are the main problems of conventional radioactive DDRT and conventional fluorescence DDRT methods, respectively.

SUMMARY OF THE INVENTION

The invention on which the present application is based provides a method which can be used for analyzing RNA samples and in particular for analyzing differentially regulated genes. This method does not suffer from the above-mentioned disadvantages.

The present invention relates to a method for analyzing an RNA sample, preferably a mRNA sample, which comprises:

a) using a first primer, which is, where appropriate, labeled with a first dye, to prepare the first strand of a complementary DNA sample (cDNA sample) from an RNA sample, preferably an mRNA sample, b) using a second primer, which is preferably labeled with a second dye, to prepare the second strand of this cDNA sample, c) using the first primer, which is labeled with a first dye, and the second primer, which is labeled with a second dye, to amplify the cDNA sample, and d) analyzing the composition of the amplified and labeled cDNA sample.

The RNA sample contains mRNA to be analyzed. In a preferred embodiment of the invention, mRNA is used in the method. The RNA can be isolated, for example, by known methods such as $CsCl_2$ density gradient centrifugation or column chromatography. The RNA is preferably isolated from a cell or a population of cells or from tissue. Where appropriate, the mRNA can be enriched from the RNA, for example by means of chromatography through an oligo (dT) column.

The method employs a first primer and a second primer. The first primer is the primer which is used for the reverse transcription. The first primer can also be designated the 5' primer since it hybridizes with the mRNA and defines the 5' end of the first strand of the complementary DNA (cDNA). The second primer is used to synthesize the second strand of the cDNA. The second primer is also designated the 5' primer since it hybridizes with the first strand of the cDNA and defines the 5' end of the second strand of the cDNA.

Where appropriate, the first primer and the second primer are labeled with a dye. The first primer is used for the reverse transcription (step a above) and for the subsequent amplification of the cDNA (step c above). The first primer, which is used for the RT reaction, is either labeled with a dye or not labeled with a dye; the latter is, for example, the case when the reverse transcriptase employed does not accept the labeled primer. The first primer is in any case labeled when it is used for amplifying the cDNA. The first primer which is used for the RT and the first primer which is used for the amplification preferably have the same sequence.

The second primer, which is used both for synthesizing the second strand of the cDNA (step b above) and for amplifying the cDNA (step c above), is preferably labeled both during the second strand synthesis and during the amplification. The second primer preferably has the same sequence on both occasions. The second strand synthesis and the amplification of the cDNA are preferably elements of one reaction such that the second primer is identical.

In preferred embodiments of the invention, the first and second primers are oligodeoxynucleotides which are composed of deoxyadenosine (dA), deoxyguanosine (dG), deoxyinosine (dI), deoxyuridine (dU), deoxythymidine (dT) and deoxycytidine (dC).

The first and/or the second primer can have a base sequence (sequence composed of adenine, guanine, cytosine and thymine; termed "sequence" in that which follows) which is complementary to the sequence(s) of one (or more) particular nucleic acid(s). A primer which is complementary to a particular sequence can hybridize with a nucleic acid which contains this complementary sequence or a sequence which is derived from this complementary sequence (that exhibits a certain homology with this complementary sequence). For example, the first primer can preferably hybridize with the mRNA. The first strand of the cDNA is generated by primer extension. A primer can also have a sequence which is identical, or essentially identical, to the sequence of a particular nucleic acid. This primer can then hybridize, under specific reaction conditions, with a nucleic acid which has a sequence which is complementary to that of the particular nucleic acid. For example, the sequence of the second primer is derived from the sequence of the mRNA, i.e. the sequence of the second primer can be identical or essentially identical to the mRNA sequence. The second primer can therefore, under specific reaction conditions, hybridize with a nucleic acid which possesses a sequence which is complementary to the sequence of the mRNA, e.g. the first strand of the cDNA.

The reaction conditions under which the first primer and the second primer hybridize with a nucleic acid are preferably specific temperature and/or buffer conditions. The temperature conditions are preferably chosen such that the primers hybridize specifically with the complementary nucleic acid sequence, so that predominantly "correct" base pairings (A-T; G-C) take place, with as few incorrect base pairings as possible. If possible, an "optimal" hybridization temperature (annealing temperature) is chosen (e.g. Sambrook et al. (1989) Cold Spring Harbor Laboratory Press). In addition to this, specific salt concentrations, in particular $Mg^{2+}$ concentrations, are chosen.

A nucleic acid from whose sequence the sequence(s) of the first and/or second primer is/are derived (i.e. to which this/these sequence(s) is/are complementary or identical or essentially identical) can, for example, be a DNA, e.g. a cDNA, a gene, or a part thereof, or an RNA, preferably an mRNA.

The second primer can possess a random base sequence, with this encompassing both primers which possess a completely random sequence and primers which possess a partially random sequence (e.g. random in relation to one or more bases). While the sequences may be random, they may at the same time exhibit a particular ratio between the individual bases, such that all the bases may occur in the same ratio or one or more bases may be over-represented or under-represented. In particular, hypoxanthine can also be used.

The second primer can also possess one or more defined base sequences. This/these defined sequence(s) may be selected randomly, i.e. they do not derive from known sequences. Primers of this nature can be used to identify new genes or proteins which have not previously been identified.

The second primer can possess a base sequence which is derived from known sequences, i.e. which corresponds entirely or partially to known sequences (i.e. which is complementary or identical or essentially identical to these sequences). For example, a primer may possess a sequence which exhibits a greater or lesser degree of congruence with a particular consensus sequence or may correspond to this sequence. This approach can be used, for example, to identify differential expression of known and/or unknown members of a particular gene family/protein family.

The second primer can possess a base sequence which is derived from a particular amino acid sequence or a consensus sequence at the amino acid level. In this case, the primers can be degenerate wherein an allowance is made for the degeneracy of the genetic code in relation to a particular amino acid sequence. The degenerate primer then constitutes a mixture of primer molecules which possess different sequences and allow for all the codon usage possibilities that encode the corresponding amino acid sequence.

The sequence of the second primer preferably possesses a restriction cleavage site for a restriction endonuclease.

The second primer can preferably have a length of from 8 to 20 nucleotides in order to ensure that hybridization is as specific as possible. However, the length is preferably selected in accordance with the particular primer sequences and/or the reaction conditions. The lengths and sequences of the first and second primer are chosen independently of each other.

The first and/or second primer(s) can also contain (a) sequence(s) which is/are not required for the hybridization and/or which does/do not contribute to the hybridization. Other sequences of this nature can, for example, make possible or facilitate the further characterization or use of the amplified cDNA. These other sequences are preferably located at the 5' end of the primer. For example, the primer may contain a sequence which facilitates subsequent sequencing such as an M13 sequence, facilitates the preparation of a labeled probe (e.g. for hybridizing in Northern blots or Southern blots and/or for hybridizing in situ), or facilitates the preparation of additional primers containing, e.g. a T7 promoter sequence, a T3 promoter sequence or an SP6 promoter sequence.

DETAILED DESCRIPTION OF THE INVENTION

In the first procedural step, the mRNA is reverse-transcribed, thereby preparing the first strand of a cDNA (step a above). A first primer, which is labeled with a dye, where appropriate, is used for the RT reaction. The first primer preferably possesses an oligo(dT) sequence, "(T)X", where 'X' indicates the number of thymidine residues. This first primer hybridizes with the poly (A) tail of each of the mRNAs and is in this way able to provide a free 3'-OH end for the polymerase reaction. The oligo (dT) sequence is preferably a sequence composed of 10–20 thymidine residues (X=10 –20), with a sequence composed of 12 thymidine residues (X=12) or 15 thymidine residues (X=15) being particularly preferred.

In a particularly preferred embodiment, the sequence of the first primer possesses, at the 3' end of the oligo (dT) sequence, at least one further nucleotide, preferably, however, two nucleotides, which does/do not belong to the oligo (dT) sequence, thus denoting that the first nucleotide which is joined on to the 3' end of the oligo (dT) sequence is different from thymidine. The first primer preferably constitutes a mixture of primer molecules which differ in the sequence of the nucleotides which do not belong to the oligo (dT) sequence. For example, the first primer can have the sequence 5'-(T)$_X$MN-3', where "M" is A (the base adenine), C (the base cytosine) or G (the base guanine) and "N" is A, C, G or T (the base thymine). For example, X can =12 or 15:

```
SEQ ID NO. 1:   5'-TTTTTTTTTTTTMN-3'(5'-
                (T)₁₂-MN-3'"),

SEQ ID NO. 2:   5'-TTTTTTTTTTTTTTTMN-3'(5'-
                (T)₁₅-MN-3'"),
``` where
"M" is A, C or G, and
"N" is A, C, G or T.

The first primer preferably constitutes a mixture of different primers which differ from each other in the sequence which does not belong to the oligo (dT) sequence. 5'-T$_{(x)}$MN-3' can be a mixture of primer molecules having the sequences:

5'-T$_{(x)}$MN-3'
5'-T$_{(x)}$CN-3'
5'-T$_{(x)}$GN-3'
    in which N=A,C,G,T
5'-T$_{(x)}$MN-3' is preferably a mixture of primer molecules having the sequences:
5'-T$_{(x)}$MA-3'
5'-T$_{(x)}$MC-3'
5'-T$_{(x)}$MG-3'
5'-T$_{(x)}$MT-3'
    in which M=A,C,G, where the possible bases A, C and G are represented uniformly in the mixture; for example, 5'-(T)$_X$MN-3' is a mixture of primer molecules having the following sequences-5'-(T)$_X$AG, 5'-(T)$_X$ CG, 5'-(T)$_X$ GG, 5'-(T)$_X$ AT, 5'-(T)$_X$ CT, 5'-(T)$_X$ GT, etc. It is possible in this way to provide primers for amplifying different mRNAs of unknown sequence. At the same time, this arrangement ensures that the primers preferentially hybridize with the 3' end of the complementary sequence, at the poly (A) tail of the mRNA.

An RNA-dependent DNA polymerase, for example the enzyme reverse transcriptase or another DNA-dependent polymerase having reverse transcriptase activity, for example, an appropriate temperature-stable polymerase which can then also be used for subsequently amplifying the cDNA (step c above) is preferably used for the RT reaction. In a particular embodiment of the invention, the synthesis of the second strand of the cDNA is an element of the procedural step for amplifying the cDNA, with the procedural step for amplifying the cDNA preferably being a PCR reaction.

The reverse transcription can, for example, be carried out at 37° C.–50° C., preferably at 40° C.–45° C., particularly preferably at 42° C. Preference is given to using a hybridization temperature which enables the first primer to hybridize specifically, with as few incorrect base pairings as possible, which ensures that the activity of the polymerase is sufficiently high and which makes it possible to obtain transcripts which are as complete as possible.

The second strand of the cDNA is synthesized using a second primer which is preferably labeled. The second primer is preferably at least 6 nucleotides in length (a 6 mer), particularly preferably from 10 (a 10 mer) to 20 (a 20 mer) nucleotides in length. In a particular embodiment of the invention, the second primer is 13 nucleotides in length (a "13 mer"). For example, the sequence of the second primer can be "(N)$_X$", where "X" is 6–20 and where "N" is A, C, G or T, independently of each other.

The first and second primers are preferably synthetic oligonucleotides which can, for example, be obtained commercially or can be synthesized on a solid phase using a known method such as the phosphoramidite method in accordance with Caruthers et al. (1983 Tetrahedron Letters 24, 245). The primers are preferably composed of the nucleotides deoxyadenosine, debxyguanosine, deoxyinosine, deoxycytidine and deoxythymidine.

In a particularly preferred embodiment of the method, the synthesis of the second strand of the cDNAs is already an element of the PCR reaction, with this strand being synthesized under the reaction conditions under which the PCR is carried out.

The first and second primers are preferably labeled differently. In principle, any type of labelling can be used, for example a primer can be coupled to digoxigenin or biotin such that a cDNA molecule which has been amplified using this primer can be detected, with an appropriate antibody or enzyme. A primer can also be coupled to a chemical compound which enables a substrate to be converted after it has been added, for example, the Atto-Phos system (JBL Scientific, San Luis Obispo, Calif., USA) or ECF substrate (Amersham-Pharmacia Biotech, Freiburg, Germany).

However, particular preference is given to labelling the first and/or second primer. fluorescently. Preference is given to labelling the first primer with a first fluorescent label and the second primer with a second fluorescent label. The first and second fluorescent labels are preferably chosen such that the two fluorescent labels employed can be clearly differentiated. In this context, the unambiguity of the result, or the detectable difference between the labelling patterns of individual cDNAs, depends both on the fluorescent labels employed and on the sensitivity of the analytical method. As a rule, computer-assisted analytical methods are used for evaluating the results. For example, the fluorescent labels can be selected such that the detectable excitation wavelengths and/or emission wavelengths of the first and second fluorescent labels differ by 200 nm or more, e.g. 250 nm, 300 nm, 350 nm or 400 nm.

Examples of fluorescent labels to which the first and/or second primer can be coupled are Cy2, Cy3, Cy5, FAM, 6-FAM (6-carboxyfluorescein (blue)), FITC (fluorescein isothiocyanate), fluorescein, HEX (4, 5, 2',4',5',7'-hexachloro-6-carboxyfluorescein (green)), 5-IAF, TAMRA (6-carboxytetramethylrhodamine (yellow)), TET (4, 7, 2', 7'-tetrachloro-6-carboxyfluorescein), XRITC (rhodamine-X-isothiocyanate), ROX (6-carboxyrhodamine (red)), Alexa488, Alexa532, Alexa546, Alexa594, Texas red and lissamine.

For example, the following combinations are possible: Primer 1 labeled with Cy5 and primer 2 labeled with Alexa488; primer 1 labeled with Cy5 and primer 2 labeled with FITC; primer 1 labeled with Cy5 and primer 2 labeled with FAM; primer 1 labeled with Cy5 and primer 2 labeled with Cy2; primer 1 labeled with Cy5 and primer 2 labeled with Cy3; primer 1 labeled with fluorescein and primer 2 labeled with Texas red; primer 1 labeled with fluorescein and primer 2 labeled with lissamine; primer 1 labeled with fluorescein and primer 2 labeled with ROX; primer 1 labeled with fluorescein-Cy3; primer 1 labeled with Alexa594 and primer 2 labeled with Alexa488; primer 1 labeled with Alexa568 and primer 2 labeled with Alexa488; primer 1 labeled with Alexa546 and primer 2 labeled with Alexa488; primer 1 labeled with Alexa532 and primer 2 labeled with Alexa488; primer 1 labeled with Texas red and primer 2 labeled with Alexa488; primer 1 labeled with ROX and primer 2 labeled with Alexa488; primer 1 labeled with Alexa488 and primer 2 labeled with lissamine; primer 1 labeled with Alexa488 and primer 2 labeled with Cy3; primer 1 labeled with Alexa488 and primer 2 labeled with ROX. Naturally, corresponding primer combinations, in which the fluorescent labels used for the labelling are transposed, with regard to primer 1 and primer 2, as compared with the above examples, are also possible.

The fluorescent labels are preferably coupled to the 5' end of the primer or oligonucleotide. In the case of an oligo (dT) primer, a further nucleotide which is different from thymidine, for example a guanosine, can be located at the 5' end in front of the fluorescent label. In addition, a fluorescence can also be coupled to the oligonucleotide by way of a base. Where appropriate, a fluorescent label can also be coupled to the first and/or second primer by way of a suitable linker.

Examples of labeled primers which can be used as the first and/or second primer are:

5'-CY5-G(T)$_{15}$MN-3', 5'-CY2-G(T)$_{15}$MN-3', 5'-CY3-G(T)$_{15}$MN-3',

5'-FAM-G(T)$_{15}$MN-3', 5'-6-FAM-G(T)$_{15}$MN-3', 5'-FITC-G(T)$_{15}$MN-3',

5'-fluorescein -G(T)$_{15}$MN-3', 5'-HEX-G(T)$_{15}$MN-3', 5'-55 -IAF-G(T)$_{15}$MN-3',

5'-TAMRA-G(T)$_{15}$MN-3', 5'-TET-G(T)$_{15}$MN-3', 5'-XRITC -G(T)$_{15}$MN-3',

5'-ROX-G(T)$_{15}$MN-3', 5'-Alexa488 -G(T)$_{15}$MN-3', 5'-Alexa532 -G(T)$_{15}$MN-3', 5'-Alexa546 -G(T)$_{15}$MN-3', 5'-Alexa594-G(T)$_{15}$MN-3', 5'-Texas red-G(T)$_{15}$MN-3', 5'-lissamine -G(T)$_{15}$MN-3' (the primers which have so far been mentioned are preferably used as first primers), 5'-CY5-(N)$_{13}$-3', 5'-CY2-(N)$_{13}$-3', 5'-CY3-(N)$_{13}$-3', 5'-FAM-(N)$_{13}$-3', 5'-6-FAM-(N)$_{13}$-3', 5'-FITC-(N)$_{13}$-3', 5'-fluorescein-(N)$_{13}$-3', 5'-HEX-(N)$_{13}$-3',

5'-5-IAF-(N)$_{13}$-3', 5'-TAMRA-(N)$_{13}$-3',5'-TET-(N)$_{13}$-3',

5'-XRITC-(N)$_{13}$-3', 5'-ROX-(N)$_{13}$-3', 5'-Alexa488-(N)$_{13}$-3',

5'-Alexa532-(N)$_{13}$-3', 5'-Alexa546-(N)$_{13}$-3',5'-Alexa594,-(N)$_{13}$-3', 5'-Texas red-(N)$_{13}$-3' and 5'-lissamine-(N)$_{13}$-3' (these primers are preferably used as second primers), where "M" is A, C or G and "N" is A, C, G or T.

When the first and/or second primer is/are fluorescently labeled, care must be taken to ensure that the excitation wavelengths are sufficiently far apart in order to be able to establish, after the excitation, to which wavelength an observable emission was due. An example of a good combination is labelling the first primer or TX-MN primer with Cy5 (excitation at 650 nm) and the second primer with a fluorescein-based label (excitation at 490 nm). The use of two differently labeled primers makes it possible to draw an unambiguous conclusion about the primer composition of (a) detected amplified cDNA(s), e.g. in a gel.

If, for example, only an emission at 650 nm can be observed, then the cDNA was amplified using the Cy5-labeled primer. Thus this cDNA has the first primer (e.g. the (T)$_X$-MN primer) at one end at least. If, on the other hand, an emission can be observed at an excitation wavelength of 490 nm, then at least one end of the cDNA was amplified with the second primer. Therefore, if a particular amplified cDNA (in the gel) only emits at one excitation wavelength, then the cDNA was only amplified using one primer, specifically the primer having a fluorescence which emits at the corresponding excitation wavelength. Consequently, if a particular amplified cDNA (in the gel) emits at two excitation wavelengths, then this cDNA was amplified using the first and/or the second primer.

The amplification, preferably PCR, is carried out using a DNA polymerase, preferably a DNA-dependent DNA polymerase, with particular preference being given to this DNA polymerase being a temperature-stable DNA polymerase such as Taq polymerase, VENT polymerase, AmpliTaq polymerase or AmpliTaq Gold polymerase, inter alia. The PCR is carried out using a temperature profile which preferably enables the cDNA to be amplified exponentially. For example, the temperature cycle quoted in Example 2 can be used for this purpose. Preference is given to running 30–40 or more cycles.

After that, the labeled and amplified cDNA is analyzed. For example, the amplified cDNA can be fractionated in a gel, with amplified cDNAs differing in length being located in different bands. Further analysis of these bands can take place, for example, in scanners which excite the fluorescent label at a given wavelength, depending on the fluorescent label employed in each case, and/or scanners which are able to detect the light which is emitted in association with the chemical transformation of a chemiluminescent substrate. The emitted fluorescent light can then, for example, be evaluated with an appropriate computer program and assembled into a gel picture as is known, for example, from autoradiographs. Examples of scanners which can be used are the FluorImager 575, Fluorimager SI, FluorImager (Molecular Dynamics, Krefeld, Germany), Strom (Molecular Dynamics), FLA-2000 (Fuji, Tokyo, Japan), FMBioII (Hitachi, through Biozym Diagnostic GmbH, Hess. Oldendorf, Germany), Fluor-S-MultiImager and Molecular Imager FX (BioRad, Munich, Germany) scanners.

The method employs, in particular, mRNA (also termed "mRNA sample") which is isolated from a cell. As a rule, a sample of this nature is a heterogeneous mRNA sample in that it contains a mixture of the mRNAs which were present in this cell at the time the RNA was isolated. As a rule, this heterogeneous mRNA sample represents the genes which were expressed by a particular cell at a particular time and under particular conditions. Thus, the composition of the mRNA sample depends, for example, on the cell type, its state of differentiation, the cell cycle and/or the previous treatment of the cell, etc.

One particular embodiment of the invention relates to the analysis of a heterogeneous mRNA sample, which comprises:
 a) using a first primer, which is, where appropriate, labeled with a first dye, to prepare the first strand of a complementary heterogeneous DNA sample or heterogeneous cDNA sample from a heterogeneous mRNA sample,
 b) using a second primer, which is preferably labeled with a second dye, to prepare the second strand of this heterogeneous cDNA sample,
 c) using the first primer, which is labeled with 2 first dye ("labeled first primer"), and the second primer, which is labeled with a second dye ("labeled second primer"), to amplify the heterogeneous cDNA sample, and
 d) analyzing the composition of the heterogeneous, amplified and labeled cDNA sample.

The genes which are especially of interest are those that are expressed by a particular cell at a particular time and are differentially expressed or regulated. In the present case, it is of particular interest to analytically compare differentially expressed genes. One particular embodiment of the invention relates to a correspondingly analogous method for analytically comparing two or more heterogeneous mRNA samples.

One particular embodiment of the invention relates to a method for analytically comparing a first heterogeneous mRNA sample with one or more additional heterogeneous mRNA samples, which comprises:
 a) using a first primer, which is, where appropriate, labeled with a first dye, for each of two or more heterogeneous mRNA samples, to prepare, in each case; the first strand of a complementary, heterogeneous DNA sample or heterogeneous cDNA sample from these mRNA samples,
 b) then using a second primer, which is preferably labeled with a second dye, to prepare, in each case, the second strand of the heterogeneous cDNA sample for each of these samples,
 c) using the first labeled primer and the second labeled primer to amplify each of the heterogeneous cDNA samples, and
 d) analyzing the composition of each heterogeneous, amplified and labeled cDNA sample and comparing the compositions of the samples.

Another particular embodiment of the invention relates to a method which comprises:
 a) using a first primer, which is, where appropriate, labeled with a first dye, for each of two or more heterogeneous mRNA samples, to prepare, in each case, the first strand of a complementary, heterogeneous DNA sample or heterogeneous cDNA sample from these mRNA samples,
 b) using a second primer, which is preferably labeled with a second dye, to prepare, in each case, the second strand of the heterogeneous cDNA sample for each of the samples,
 c) using the first labeled primer and the second labeled primer to amplify each of the heterogeneous cDNA samples, and
 d) carrying out an analysis to determine which of the samples does/do contain or not contain individual mRNA molecules.

After the cDNA has been amplified and the composition of the cDNA has, where appropriate, been analyzed, an investigation is carried out to determine which of the amplified cDNAs have which primer composition. For example, determination of which cDNAs were amplified using only the first primer, which were amplified using only the second primer, and which were amplified using the first and the second primers is carried out to affiliate each of the differentially amplified cDNAs to products 1 to 4 above. The invention also relates to follow-up methods in which particular amplified cDNAs are selected on the basis of the primer composition of the amplified cDNAs and, where appropriate, subjected to further analysis and/or further use. In addition to this, the invention relates to follow-up methods in which the distribution of the primer composition of the totality of the amplified cDNAs is analyzed with regard to products 1 to 4 as described above.

Examples of follow-up methods are:
1. A method for analyzing an RNA sample, preferably an mRNA sample, which comprises:
 a) using a first primer, which is, where appropriate, labeled with a first dye, to prepare the first strand of a complementary DNA sample or cDNA sample from an RNA sample, preferably an mRNA sample,
 b) using a second primer, which is preferably labeled with a second dye, to prepare the second strand of this cDNA sample,
 c) using the first primer, which is labeled with a first dye, and the second primer, which is labeled with a second dye, to amplify the cDNA sample, and
 d) analyzing the composition of the amplified and labeled cDNA sample, and
 e) determining the primer composition of amplified cDNAs.
2. A method for analyzing an RNA sample, preferably an mRNA sample, which comprises:
 a) using a first primer, which is, where appropriate, labeled with a first dye, to prepare the first strand of a complementary DNA sample or cDNA sample from an RNA sample, preferably an mRNA sample, b) using a second primer, which is preferably labeled with a second dye, to prepare the second strand of this cDNA sample, c) using the first primer, which is labeled with a first dye, and the second primer, which is labeled with a second dye, to amplify the cDNA sample, and d) analyzing the composition of the amplified and labeled cDNA sample, e) determining the primer composition Of amplified cDNAs, and f) selecting cDNAs having a particular primer composition, preferably those cDNAs which contain both the first and the second primer, and subjecting them to further analysis.

The RNA or mRNA samples which are used for the comparative analysis or methods can, for example, be isolated from different cells whose expression patterns are to be compared with each other. In this context, the mRNA samples can, for example, be mRNA samples which are derived from different cells or cell types which differ from each other in their stage of differentiation and/or development or in the stage of the cell cycle. Additionally, these cells or cell types can have a history of different culture conditions such as pH, temperature, or composition, exposure to pharmacological active compounds, or exposure to disease-promoting/disease-inhibiting or disease-inducing substances such as carcinogenic or mutagenic substances or UV light. Such RNA or mRNA samples can be compared with RNA or mRNA samples which have not been exposed, or not exposed to this extent, to these substances. The RNA or mRNA samples can be isolated from particular tissues. For example, healthy tissue can be compared analytically with pathological tissue, young tissue with old tissue, treated tissue with untreated tissue, and induced tissue with non-induced tissue, while tissues from different stages of development and/or the cell cycle and/or differentiation can also be compared analytically, with tissue denoting tissue, organ, cell type, culture-derived cells, cells of a cell line or the cells of an individual.

For example, the method can be used for analyzing differential gene expression in a tissue or in a cell. In particular, the method can be used for analytically comparing differential gene expression in two or more tissues or cells.

The method can be used for identifying and/or characterizing pharmacologically active compounds. Furthermore, the method can be used for identifying and/or characterizing target genes or target proteins. These target genes or target proteins are, in particular, genes or proteins which have a function (which is as specific as possible) in the prevention, origin and/or progress and/or healing of a disease, in the differentiation process, for instance cell differentiation where appropriate, before or after induction and/or in the differentiation process of a disease, in the cell cycle or cell cycle control and/or cell development as in the process of cell aging.

The method is seen to be advantageous in comparison with conventional radioactive DDRT since the use of fluorescence-labeled primers can be substituted for the use of radioactively labeled nucleotides or radioactively labeled primers. In the novel method (DDRT variant) which is described here, in contrast to the known fluorescence DDRTs, each amplified cDNA is labeled by using two primers which are differentially labeled, preferably with fluorescent labels having different excitation spectra. In this way, by using an appropriate evaluation method, it is possible to detect each amplified, labeled cDNA. The band complexity of the amplified cDNA is retained and is detectable as products 1, 2, 3, and 4 in the gel. In addition to this, it is possible to draw unambiguous conclusions about the primer composition of an amplified labeled cDNA and assign the cDNA to product 1, 2, 3 and 4. This makes it possible to select the cDNAs which are to be subjected to further analysis because of their primer composition. For example, it is possible to select amplified cDNAs which actually do derive from the 3' regions of the gene sequences. When this method which is based on using two differently labeled primers is employed, it is possible to reduce the time and expense involved in possibly having to isolate and analyze redundant cDNAs. Despite this, all the amplified cDNAs are detected, and can be analyzed, simultaneously, as in conventional radioactive DDRT, which is a feature not afforded in conventional fluorescence DDRT.

The invention also relates to a test kit for implementing the method.

EXAMPLES

The enzymes employed are obtained from Gibco BRL/Life Technologies (Karlsruhe, Germany) (reverse transcriptase and Taq polymerase) and Promega (Heidelberg) (RNAsin). Thermocycler: Perkin Elmer GeneAmp PCR System 2400 (Perkin Elmer, Weiterstadt).

Example 1

Reverse Transcription

Reaction mixture: 1 $\mu$l of RNA (100 ng-1 $\mu$g of total RNA or 1 ng–10 ng of poly-A-RNA/mRNA), 1 $\mu$l of primer 1 (10 $\mu$M primer 1, e.g. $(T)_X$-MA-3' or Cy5-$(T)_X$MA-3', where M=A, C, G and X=11–15), and 8 $\mu$l of H$_2$O (nuclease-free). The reaction mixture was incubated at 70° C. for 5 min and then placed on ice. 4 $\mu$l of 5-times RT buffer (Gibco BRL), 2 $\mu$l of DTT [0.1 M],1 $\mu$l of SuperScript reverse transcriptase [200 U/$\mu$l] (Gibco BRL),1 $\mu$l of RNAsin [40 U/$\mu$l] and 2 $\mu$l of dNTP [250 $\mu$M] were then added. The reverse transcription was carried out at 37°–50° C. for 60 min and the enzyme was then inactivated at 70° C. (10 min).

Example 2

PCR

2 $\mu$l of 10-times PCR buffer (Gibco BRL), 0.9 $\mu$l of W-1 detergent [1%] (Gibco BRL), 0.75 $\mu$l of MgCl$_2$ [50mM] (Gibco BRIL), 1.6 $\mu$l of dNTP [250 $\mu$M], 0.5 $\mu$l of Taq DNA polymerase [5 U/$\mu$l] (Gibco BRL), 1 $\mu$l each of primer 1 and primer 2 ([10$\mu$M]; e.g. Cy5-T7-$(T)_X$-MA-3' as primer 1 (where "T7" is a sequence segment from the T7 promoter) and fluorescein-$(N)_X$, where X=10–25 and N=A, C, G, T) and 10.25 $\mu$l of H$_2$O were added to 2 $\mu$l of the RT mixture from Example 1.

The PCR was carried out under the following conditions:

```
       5 min at 94° C.
40×:   1 min at 94° C.,    2 min at 40° C.–60° C.,   1 min at 72° C.
       7 min at 72° C.
```

After the conclusion of the PCR, the reaction mixture is stored at 4° C. and then fractionated on a sequencing gel. (5% polyacrylamide; 8 M urea).

The labeled amplified cDNAs can be detected, for example, using a scanner which excites at a wavelength of 430 +/−30 nm (for fluorescein: excitation wavelength 490 nm, emission wavelength 520 nm) and 635 +/−5 nm (for Cy5: excitation wavelength 650 nm, emission wavelength 675 nm). The Molecular Dynamics Storm Imager is an example of this type of scanner.

The publications and patents cited herein are incorporated by reference in their entirety.

Ito T. et al. (1994) Fluorescent Differential Display: Arbitrarily Primed RT-PCR Fingerprinting on an Automated DNA Sequencer. *FEBS Letters* 351:231–236.

Ito T. et al. (1997) Differential Display Methods and Protocols. *Methods in Molecular Biology*. 85:37–44.

Jones, S. W. et al. (1997) Generation of Multiple mRNA Fingerprints Using Fluorescence-based Differential Display and an Automated DNA Sequencer. *Biotechniques*. 22:536–543.

Liang P. et al., (1992) Differential Display of Eukaryotic Messenger RNA by Means of the Polymerase Chain Reaction. *Science*. 257:967–971.

Liang P. et al. (1995) Recent Advances in Differential Display. *Cur. Opin. Imm.* 7:274–280.

McClelland M. et al. (1995) RNA Fingerprinting and Differential Display Using Arbitrarily Primed PCR. *Trends in Genetics* 11:242–246.

Sambrook et al. (1989) Molecular Cloning, A Laboratory Manual. $2^{nd}$ edition. Cold Spring Harbor Laboratory Press.

Smith N. R. et al. (1997) Automated Differential Display Using a Fluorescently Labeled Universal Primer. *Biotechniques*. 23:274–279.

b) using a second primer, which is labeled with a second dye, to prepare the second strand of this cDNA sample, c) using the first primer, which is labeled with a first dye, and the second primer, which is labeled with a second dye, to amplify the cDNA sample, and d) analyzing the composition of the amplified, labeled cDNA sample to identify pharmacologically active compounds.

2. The method of claim 1, wherein the first primer contains an oligo (dT) sequence.

3. The method of claim 2, wherein the oligo (dT) sequence of the first primer is composed of at least 10 thymidine nucleotides.

4. The method of claim 3, wherein the first primer contains, at the 3' end of the oligo (dT) sequence, at least two further nucleotides, which do not belong to the oligo (dT) sequence.

5. The method of claim 4, wherein the first primer is a heterogeneous mixture of primer molecules which differ in the sequence of the nucleotides which are in positions M or N and which do not belong to the oligo (dT) sequence.

6. The method of claim 1, wherein the second primer is at least 6 nucleotides in length.

7. The method of claim 6, wherein the first and second dyes are of different fluorescences.

8. The method of claim 7, wherein the fluorescences are selected from fluorescences Cy2, Cy3, FAM, 6-FAM, FITC, fluorescein, HEX, 5-IAF, TAMRA, TET, XRITC, ROX, Alexa488, Alexa532, Alexa546, Alexa594, Texas red, and lissamine.

We claim:

1. A method for identifying and characterizing pharmacologically active compounds comprising analyzing an RNA sample by:

a) using a first primer, which is labeled with a first dye, to prepare the first strand of a complementary DNA sample (cDNA) sample from an RNA sample, 9. The method of claim 1, wherein apart from the first RNA sample, one or more additional RNA samples are compared analytically.

10. A method for identifying and characterizing pharmacologically active compounds comprising analyzing an RNA sample by:

a) using a first primer, which is labeled with a dye, to prepare the first strand of a complementary DNA sample (cDNA) sample from an RNA sample,
b) using a second primer to prepare the second strand of this cDNA sample,
c) using the first primer, which is labeled with a dye, and the second primer to amplify the cDNA sample, and
d) analyzing the composition of the amplified, labeled cDNA sample to identify pharmacologically active compounds.

11. The method of claim 10, wherein the first primer contains an oligo (dT) sequence.

12. The method of claim 11, wherein the oligo (dT) sequence of the first primer is composed of at least 10 thymidine nucleotides.

13. The method of claim 12, wherein the first primer contains, at the 3' end of the oligo (dT) sequence, at least two further nucleotides, which do not belong to the oligo (dT) sequence.

14. The method of claim 13, wherein the first primer is a heterogeneous mixture of primer molecules which differ in the sequence of the nucleotides which are in positions M or N and which do not belong to the oligo (dT) sequence.

15. The method of claim 10, wherein the second primer is at least 6 nucleotides in length.

16. The method of claim 10, wherein the dye is a fluorescence.

17. The method of claim 16, wherein the fluorescence is selected from fluorescences Cy2, Cy3, FAM, 6-FAM, FITC, fluorescein, HEX, 5-IAF, TAMRA, TET, XRITC, ROX, Alexa488, Alexa532, Alexa546, Alexa594, Texas red, and lissamine.

18. The method of claim 10, wherein apart from the first RNA sample, one or more additional RNA samples are compared analytically.

* * * * *

UNITED STATES PATENT AND TRADEMARK OFFICE
CERTIFICATE OF CORRECTION

PATENT NO. : 6,645,741 B2
DATED : November 11, 2003
INVENTOR(S) : Detlef Kozian et al.

It is certified that error appears in the above-identified patent and that said Letters Patent is hereby corrected as shown below:

Column 13,
Lines 63-64, "an RNA" should read -- a RNA --.
Line 67, "an RNA" should read -- a RNA --.

Column 14,
Line 15, "nucleotides, which" should read -- nucleotides, M and/or N, which --.
Lines 66-67, "an RNA" should read -- a RNA --.

Column 15,
Line 3, "an RNA" should read -- a RNA --.
Line 18, "nucleotides, which" should read -- nucleotides, M and/or N, which --.

Signed and Sealed this

Twenty-ninth Day of June, 2004

JON W. DUDAS
*Acting Director of the United States Patent and Trademark Office*

SEQUENCE LISTING

```
<160> NUMBER OF SEQ ID NOS: 2

<210> SEQ ID NO 1
<211> LENGTH: 14
<212> TYPE: DNA
<213> ORGANISM: Artificial Sequence
<220> FEATURE:
<221> NAME/KEY: exon
<222> LOCATION: (1)..(14)
<223> OTHER INFORMATION: Description of Artificial Sequence: synthetic
      "V=A,C,G; N=A,C,G,T"

<400> SEQUENCE: 1 ttttttttt ttvn                                                     14

<210> SEQ ID NO 2
<211> LENGTH: 17
<212> TYPE: DNA
<213> ORGANISM: Artificial Sequence
<220> FEATURE:
<221> NAME/KEY: exon
<222> LOCATION: (1)..(17)
<223> OTHER INFORMATION: Description of Artificial Sequence: synthetic
      "V=A,C,G; N=A,C,G,T"

<400> SEQUENCE: 2 ttttttttt tttttvn                                                  17
```